United States Patent [19]
Reid et al.

[11] Patent Number: 5,681,931
[45] Date of Patent: Oct. 28, 1997

[54] HUMAN RESTRICTIN

[75] Inventors: Robert Alan Reid, Durham; Rhonda Lucille Ackley, Chapel Hill; John Jacob Hemperly, Apex, all of N.C.

[73] Assignee: Becton, Dickinson and Company, Franklin Lakes, N.J.

[21] Appl. No.: 404,781

[22] Filed: Mar. 15, 1995

[51] Int. Cl.$^6$ .................................................. C07K 14/47
[52] U.S. Cl. .......................................................... 530/350
[58] Field of Search ........................... 530/388.2, 389.1; 435/240.27, 70.21, 172.2

[56] References Cited

U.S. PATENT DOCUMENTS 4,289,690  9/1981  Pestka .

FOREIGN PATENT DOCUMENTS 0386752  12/1990  European Pat. Off. .

OTHER PUBLICATIONS

Fuss, I. Cell Biology 120: 1237–1249, 1993.
Norenberg, Neuron 8:849–863, 1992.
Lipford and Wright, Cancer Research 51:2296–2301, 1991.
Kruse et al., Nature 311:153–155, 1984.
Fuss, J. Neuro Sci. Res 29:299–307, 1991.
Peshera, J. Cell Biology 109:1765–1778, 1989.
Morganti, Exp. Neurology 109:98–110, 1990.
M. Schachner, et al. "The Perplexiing Multifunctionality of Janusin, a Tenascin–Related Molecule" *Perp. Dev. Neurobiol.* 2:33–41 (1994).
F. G. Rathjen, et al. "Restrictin: a chick neural extracellular matrix protein involved in cell attachment copurifies with the cell recognition molecule F11" *Development* 113:151–164 (1991).
A. Lochter, et al. "The Extracellular Matrix Molecule Janusin Regulates Neuronal Morphology in a Substrate–and Culture Time–dependent Manner" *Euro. J. Neurosci.* 6:597–606 (1994).
P. Pesheva, et al. "Tenascin–R (J1 160/180) inhibits fibronectin–mediated cell adhesion –functional relatedness to tenascin–C" *J. Cell Sci.* 107:2323–2333 (1994).
L. Vaughan, et al. "Tenascin–Contactin/F11 Interactions: A Clue for Developmental Role?" *Persp. Dev. Neurobiol.* 2:43–52 (1994).
R. Chiquet–Ehrismann, et al. "The Tenascin Gene Family" *Persp. Dev. Neurobiol.* 2:3–7 (1994).

*Primary Examiner*—Lila Feisee
*Assistant Examiner*—Nancy A. Johnson
*Attorney, Agent, or Firm*—Donna R. Fugit

[57] ABSTRACT

Human restrictin proteins and nucleic acid sequences encoding them are provided. Antibodies which recognize human restrictin in human brain are disclosed. In the human brain, restrictin occurs as two major polypeptides of 180 and 160 kD located in fiber tracts. These polypeptides are similar to those seen in rat brain. Surprisingly, restrictin has also been found in the peripheral nerves of rats and humans. The antibodies also detect a 170 kD polypeptide in MATRIGEL, an extracellular matrix product of rat EHS sarcoma cells widely used as a tissue culture substrate. Monoclonal antibodies to human restrictin and assays using the human restrictin protein, antibodies and DNA sequences are also provided.

1 Claim, 1 Drawing Sheet

HUMAN RESTRICTIN

FIELD OF THE INVENTION

The present invention relates to extracellular matrix molecules and nucleic acid sequences encoding them.

BACKGROUND OF THE INVENTION

The adherence of cells to each other and to the extracellular matrix, as well as the cellular signals transduced as a consequence of such binding, are of fundamental importance to the development and maintenance of body form and function. A number of molecules mediating cell adhesion have been identified and characterized at the molecular level both in vertebrates and in invertebrates. Many cell surface cell adhesion molecules (CAMs) are of three major types: 1) members of the immunoglobulin supergene family, which mediate calcium independent adhesion, 2) cadherins, which mediate calcium-dependent adhesion and are important structural components of adherence junctions, and 3) integrins, a family of heterodimeric proteins which can facilitate adhesion of cells both to each other and to the extracellular matrix.

CAMs may have multiple ligands. They can mediate adhesion by the interaction of a CAM on one cell with the identical CAM on another cell (homophilic binding), or they can mediate adhesion by interacting with different CAMs or extracellular matrix molecules (heterophilic binding). For example, contactin, a member of the immunoglobulin gene superfamily, can undergo homophilic binding or can bind heterophilically to other cell surface molecules such as the L1 antigen or to extracellular matrix molecules of the tenascin family. One extracellular matrix ligand for contactin is janusin, which is a member of the tenascin-R family. Janusin is closely related to tenascin in its patterns of epidermal growth factor, fibronectin type III and fibrinogen-like domains. In rodents, it is synthesized by oligodendrocytes and subpopulations of neurons at late developmental stages in the central nervous system. It can promote cell adhesion or anti-adhesion, depending on the neural cell type with which it interacts, promoting neurite outgrowth of some neural cell types and inhibiting neurite outgrowth from other neuronal populations. The repulsive response of neurons to janusin may be mediated by contactin. Janusin has been identified in rodents (A. Faissner. et al. 1990. *J. Neurochem.* 54: 1004–1015) and the rat gene has been cloned (B. Fuss, et al. 1991. *Neurosci. Res.* 29:299–307) and sequenced (B. Fuss, et al. 1993. *J. Cell Biol.* 120:1237–1249). The chicken homolog of janusin, referred to as restrictin, has also been identified and characterized (U. Norenberg, et al. 1992. *Neuron* 8:849–863).

SUMMARY OF THE INVENTION

Prior to the present invention, no human homolog of janusin/restrictin had been identified and it was not previously known if such a homolog existed. A human homolog of rat janusin has now been found, and the complete cDNA sequence encoding it has been determined. Antisera were prepared against a fragment of the human restrictin protein expressed in bacteria. These antibodies detect the immunogen, high molecular weight polypeptides in human brain, and cross react with several animal species. In the human brain, restrictin occurs as two major polypeptides of 180 and 160 kD located in fiber tracts. These polypeptides are similar in size to those seen in rat brain. Surprisingly, restrictin has also been found in the peripheral nerves of rats and humans. The antibodies also detect a 170 kD polypeptide in MATRIGEL, an extracellular matrix product of rat EHS sarcoma cells widely used as a tissue culture substrate. Monoclonal antibodies to human restrictin and assays using the human restrictin protein, antibodies and DNA sequences are also provided.

Figure 1:
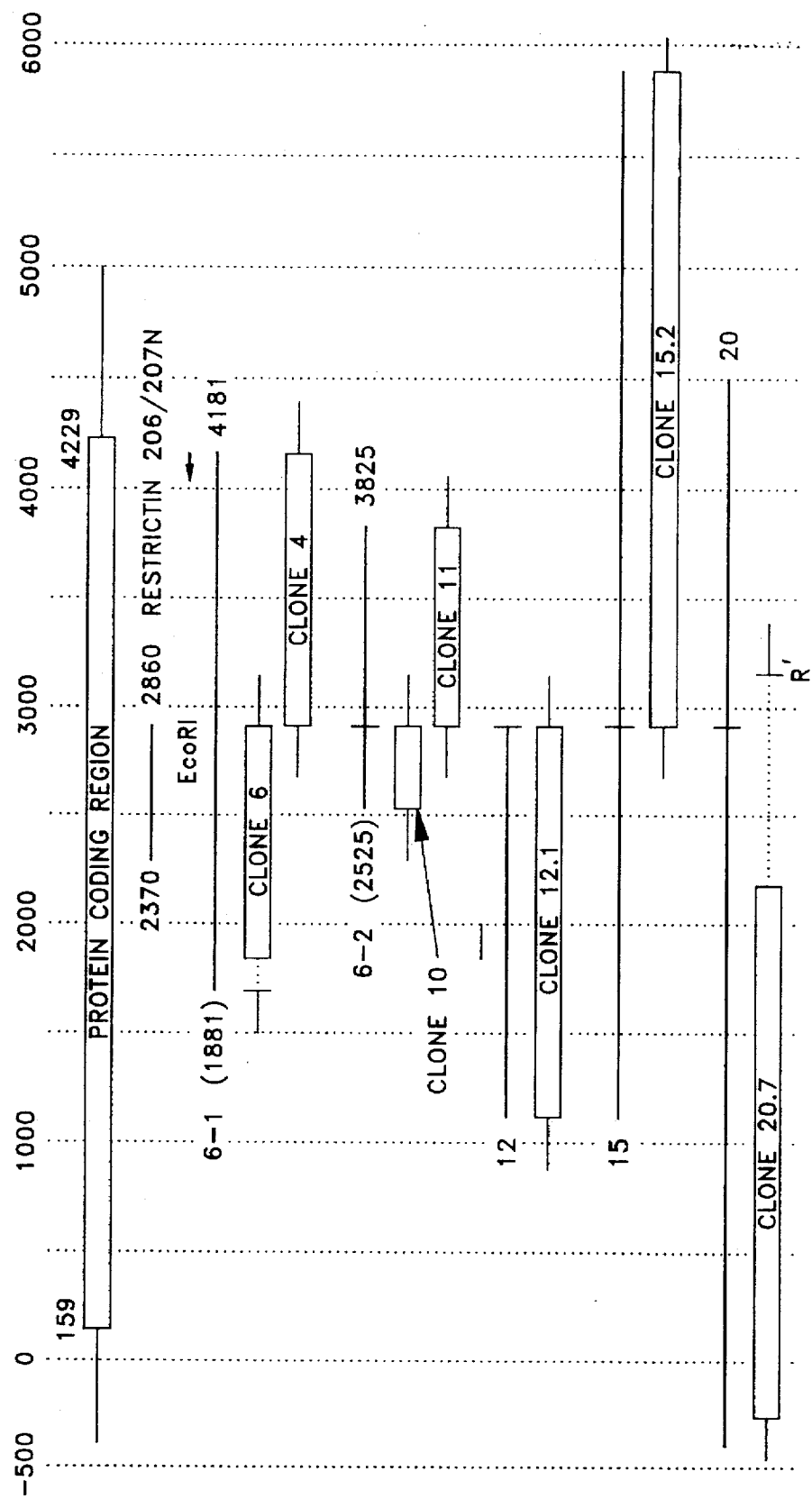
FIG. 1 illustrates the cloning process used to obtain the human restrictin cDNA sequence.

DETAILED DESCRIPTION OF THE INVENTION cDNAs encoding human restrictin were cloned from human brain polyA+ RNA using the reverse transcriptase polymerase chain reaction (RT-PCR) with primers based on the rat janusin gene sequence. RT-PCR was performed on rat and human (adult and fetal, Clontech) brain polyA+ RNA using the one-step protocol described by Goblet, et al. (1989. *Nucl. Acids Res.* 17:2144). PolyA+RNA (1 µg) and 300 ng of each primer (see below) in 66 µl DEPC water were incubated at 65° C. for 15 min. and cooled on ice. Thirty-three µl of 3×RT-PCR reagent mix (3× PCR buffer, 150 mM KCl, 30 mM Tris-HCl pH 8.3, 4.5 mM $MgCl_2$, 0.3% gelatin, 500 µM dNTPs, 200 U M-MLV reverse transcriptase, 4 U rRNAsin (Promega, Madison, Wis.), 2.5 U AMPLITAQ (Perkin-Elmer Cetus, Norwalk, Conn.) was added and the reaction was incubated at 37° C. for 30 min. The amplification reaction (94° C. for 1 min., 50° C. for 2 min., and 72° C. for 2 min.) was repeated for 40 cycles. The primer pair for amplification was as follows:

| | |
|---|---|
| 5'-ACTGACAGATCTAGAGCC | SEQ ID NO:1 (corresponding to nucleotides 2375–2392 in rat) |
| 5'-GGTGGTCGATAGGATACT | SEQ ID NO:2 (corresponding to nucleotides 2856–2839 in rat) |

A major 480 bp amplification product was obtained from rat RNA, which was subcloned and sequenced, confirming that this product corresponded to rat janusin. A minor 290 bp product was also obtained in rat. An amplification product of the appropriate size (480 bp) was also generated from human adult brain RNA. This product was subcloned and sequenced directly (Mihovilovic, 1989). Amplification of fetal RNA produced only a 290 bp amplification product which was subsequently found not to be human restrictin.

The 480 bp human amplification product (206/207N) was used as a probe on Northern blots of multiple regions of human brain (Clontech). The radiolabeled probe was prepared using a random primer labeling kit (BRL, Gaithersburg, Md.) with purification over NICK columns (Pharmacia, Piscataway, N.J.). Blots were reprobed with a human beta-actin probe (Clontech) to determine the relative amounts and integrity of RNA in each sample. The probe hybridized to a single approximately 12 Kb nucleic acid sequence in amygdala, caudate nucleus, corpus collusum, hippocampus, hypothalamus, substantia nigra, subthalamic nuclei and thalamus. The restrictin cDNA clones described below were also used as probes on northern blots of human fetal tissues. The approximately 12 Kb restrictin mRNA seen in adult brain was also detected in fetal brain, but was absent from fetal heart, lung, liver and kidney. This illustrates the tissue specificity of restrictin.

Two commercially available lambda human cDNA libraries were screened as recommended by the manufacturer using 206/207N as a probe to identify additional clones for determination of the sequence of the full-length human restrictin gene (FIG. 1). Initial screening with 206/207N identified cDNA clones 6-1 and 6-2. A second hybridization screening using a probe from the 5' end of clone 6-1, as illustrated in FIG. 1, produced cDNA clones 12 and 15. The upstream end of clone 12 was used in a third library screen to isolate clone 20. Together, these clones encode the entire protein coding region of human restrictin (FIG. 1) The lambda cDNA inserts of these clones were either 1) PCR amplified using lambda gt10 EcoRI forward and reverse primers for direct sequencing as described above (Mihovilovic, 1989), or 2) subcloned into pBLUESCRIPT (SK+) (Stratagene, La Jolla, Calif.) for sequencing by dye-termination or dye-labeled primer methods (Applied Biosystems, Model 373A, Foster City, Calif.). Sequencing primers were synthesized on an Applied Biosystems (ABI) Model 380B DNA synthesizer and purified using OPC cartridges (ABI). Sequence alignments, translations, and feature location were performed using IG-Suite software (Intelligenetics, Mountain View, Calif.). In this manner, the entire 4,724 bp human restrictin cDNA coding sequence was determined by sequencing both strands of the cDNAs (SEQ ID NO:3). The sequence of the full-length restrictin protein (1358 amino acids, SEQ ID NO:4) was deduced from the cDNA sequence. The human restrictin protein shows structural similarity to other members of the tenascin-R family. In particular, human restrictin, like its homologs from rat and chicken, comprises a short amino terminal region followed by heptad repeats, epidermal growth factor-like repeats, nine fibronectin type III repeats and a carboxyl-terminal region homologous to the globular domain of fibrinogen. There is no evidence for a hydrophobic membrane spanning region, consistent with restrictin being a secreted, extracellular matrix molecule. The human sequence obtained is highly homologous to the rat and chicken sequences at both the DNA (88 and 76%, respectively, within the protein coding region) and at the amino acid level (93 and 72%, respectively).

SEQ ID NO:3, a fragment of SEQ ID NO:3, or an equivalent nucleic acid molecule which employs degenerate codons to encode the amino acid sequence of SEQ ID NO:4 or a fragment thereof, may be cloned into an expression vector as is known in the art to produce recombinant human restrictin in transformed or transfected host cells. Recombinant human restrictin and recombinant human restrictin fragments provide a convenient source of these molecules for immunization, immunoassays, and use in tissue culture growth substrates. To generate antisera to human restrictin, the 206/207N fragment (nucleotides 2686–3165 of SEQ ID NO:3 with EcoRI cloning sites at both the 5' and 3+ ends) was subcloned into the EcoRI site of pGEX-3X (Pharmacia), producing a recombinant human restrictin-glutathione-S-transferase (GST) fusion protein for immunization. After transformation of E. coli, expression of the fusion protein was induced with IPTG and the soluble material was purified over a glutathione-S Sepharose affinity column. The purified material was used to immunize rabbits using standard methods. Sera were collected and assayed by immunoblotting against the immunogen and against the 206/207N protein fragment, expressed by subcloning into the pATH expression system (New England BioLabs). The anti-fusion protein antisera recognized both of these antigens on Western blots, but anti-chicken restrictin did not, indicating immunological differences between the human and chicken restrictin proteins.

To verify the reactivity of the antisera against human proteins, adult brain membranes were prepared and extracted. In brief, postmortem human brain was Dounce homogenized into 0.32M sucrose, 5 mM EDTA, 20 mM Tris-HCl (pH 8) containing 1 mM PMSF, 0.5 mM p-chloromercuriphenylsulfonic acid and 5 µg/ml of aprotinin and leupeptin as protease inhibitors. After centrifugation at 500×g for 30 min. to remove nuclei and cellular debris, the supernatant was centrifuged at 80,000×g to collect the membrane fraction, which was then extracted with 1% sodium deoxycholate in homogenization buffer for 1.5 hr. at 4° C. The detergent extract was clarified by centrifugation at 100,000×g and used subsequently for either SDS-PAGE directly or for further purification of a protein fraction bearing the HNK-1 epitope, which may be involved in binding cell adhesion molecules. HNK-I brain fractions were immunoaffinity enriched on anti-Leu7 (Becton Dickinson) coupled to Sepharose. Immunoblotting was performed using a PROTOBLOT AP system (Promega) as recommended by the manufacturer with an alkaline phosphatase-conjugated anti-rabbit IgG as the secondary antibody and color development using NBT/BCIP. In Western blots, the anti-fusion protein antisera routinely detected two bands of approximately 180 and 160 kD in human brain and in HNK-1 enriched fractions. These bands were apparently enriched in the latter. The reactivity of the antisera was inhibited in a concentration dependent manner by addition of the GST fusion protein, but not by addition of GST, indicating a specific immune reaction to the human restrictin fragment. Western blots of rat, mouse, cow, pig and chicken brain extracts demonstrated similar sized bands (180 kD and 160 kD) in all cases. There were, however, slight mobility shifts, possibly due to species variation in amino acid sequence or to differential glycosylation. MATRIGEL (Collaborative Biomedical Products), an extracellular matrix substrate derived from rat EHS sarcoma cells as an in vitro tissue culture growth substrate, was also reactive with the antiserum, revealing a 170 kD polypeptide.

For immunohistological studies, frozen human or rat tissues were sectioned and fixed using acetone or 4% paraformaldehyde. Staining was performed using the VECTA-STAIN ELITE ABC system (Vector Laboratories) as recommended. Primary anti-fusion protein antisera were used at a 1:1000 dilution. Paraffin sections were treated using the microwave antigen retrieval system (U.S. Pat. No. 5,244,787) before staining. The antisera were reactive with frozen sections of human peripheral nerve (peripheral nervous system), rat hippocampus (central nervous system) and human cerebellum (central nervous system) and with paraffin section human pons (central nervous system). In all cases, there were areas of clear positivity as well as areas that were clearly negative. For example, in the peripheral nerve experiments, the surrounding, non-neuronal tissue was unstained, and in the central nervous system, there were clearly unstained cells in all areas examined.

Antibodies according to the invention which recognize human restrictin are useful in methods for detecting the protein in immunoassay systems. Polyclonal antisera raised to human restrictin or to protein fragment of human restrictin may be used to detect the restrictin protein in immunoassay methods involving binding between the protein or fragment and the antibodies, e.g., ELISAs and immunoblots. These conventional immunoassay methods can be readily adapted to employ the antibodies and restrictin protein disclosed herein. Alternatively, monoclonal antibodies which recognize the human restrictin protein of the invention may be prepared using methods known in the art, such as that of Kohler and Milstein (1975. Nature 256:495) and used in immunoassays. The spleen cells of mice immunized with the human restrictin protein or a fragment thereof are fused with murine myeloma cells and the resulting hybridomas are screened against the immunogen to select those producing the desired anti-restrictin monoclonal antibody. In general, binding between protein and antibody in an immunoassay is detected by inclusion of a detectable label in the reaction which generates a signal. The detectable label is usually conjugated to the antibody or protein and may be directly detectable (e.g., a dye, radioisotope or fluorochrome) or rendered detectable after further chemical reaction (e.g., an enzyme which reacts to produce a colored product, or biotin which may be bound to labeled avidin).

Polyclonal and monoclonal antibodies according to the invention may also be used to purify human restrictin from tissues, or to purify restrictin from the tissues of a cross-reacting species by immunoaffinity purification methods, e.g., immunoaffinity chromatography. This provides a source of natural restrictin for use in immunoassays, as an immunogen, or in tissue culture systems to promote or inhibit neurite outgrowth.

Oligonucleotides derived from the nucleotide sequences encoding human restrictin are useful in nucleic acid hybridization assays for detection of related restrictin nucleotide sequences. They may also be used as primers for amplification of restrictin target sequences. Oligonucleotide probes for hybridization according to the invention may comprise the complete coding sequence of the human restrictin cDNA or a portion thereof, such as nucleotides 2686–3165 of SEQ ID NO:3. Primers are generally short portions of the nucleotide sequence which specifically hybridize to restrictin nucleotide sequences, allowing specific amplification. One skilled in the art will further recognize that oligonucleotide probes and primers may also be designed which comprise all or a portion of a sequence which is complementary to SEQ ID NO:3. Detection of nucleic acids by hybridization to a probe is known in the art. Such methods as Southern blotting, Northern blotting, dot blotting, nucleic acid amplification methods and the like may be readily adapted to detection of nucleotide sequences containing all or part of the human restrictin coding sequence, or to detection of all or part of the restrictin coding sequence of a cross-reacting species. This is done using the nucleotide sequence given in SEQ ID NO:3 to design appropriate probes and primers. For purposes of the present invention, the terms "encoding" and "coding for" are intended to include nucleic acids which comprise sequences which can be transcribed and/or translated to produce restrictin, or a fragment thereof, including degenerate nucleotide sequences. It will also be understood that probes and primers derived from the disclosed nucleotide sequences may also be used to detect fragments of restrictin coding sequences. Hybridization of the probe or amplification by the primers may be detected by means of a directly or indirectly detectable label associated with the probe or primer, i.e., incorporated into the probe or conjugated to it. In general, the same labels useful for labeling antibodies and antigens may be used to label oligonucleotides. In addition, it is within the ordinary skill in the art, given the nucleotide sequence of SEQ ID NO:3. to derive the complementary nucleotide sequence, which may also be used to prepare probes and primers and which may be detected by use of probes and primers. Further, the present disclosure of SEQ ID NO:3 allows derivation of RNA sequences which are complementary to SEQ ID NO:3 or to the complement of SEQ ID NO:3. Such equivalent RNA sequences may be detected by hybridization or amplification as well.

The reagents for performing these immunoassays, hybridization assays, and nucleic acid amplification may be conveniently packaged together for sale or use in the form of a kit. A kit for immunoassay may contain an antibody which recognizes and binds to restrictin. The antibody may be labeled, or a second antibody carrying the label may be included for detection of binding. Optionally, any reagent required for performing the assay and detecting the label may be included. A kit for hybridization assays or amplification may contain oligonucleotide probes or primers which hybridize to one or more nucleotide sequences contained in SEQ ID NO:3. The probes or primers may be conjugated to a detectable label for detection. Optionally, the hybridization or amplification kit may contain any reagents required for performing the hybridization or amplification and detecting the label.

The foregoing disclosure is intended to illustrate the invention and is not to be construed as limiting its scope as defined by the appended claims. Upon reading the present disclosure, certain equivalents and variations will be apparent to one skilled in the art without exercise of inventive skill. Such equivalents and variations are intended to be included within the scope of the invention.

What is claimed is:

1. A purified protein consisting of the amino acid sequence of SEQ ID NO:4.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:1:

ACTGACAGAT CTAGAGCC   18

( 2 ) INFORMATION FOR SEQ ID NO:2:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

```
GGTGGTCGAT AGGATACT                                                    18
```

( 2 ) INFORMATION FOR SEQ ID NO:3:

( i ) SEQUENCE CHARACTERISTICS:
    ( A ) LENGTH: 4724 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:3:

```
GAATTCCGGG AGAAGGGGGT CCTCTCTGAC CCAAGGAATT ACCACTAGTG GAGTGAAGCC      60
ACCTGACTTT TTGATCTTAT TTTGGTTGCC TCCTCATTCT CCTTCCACCC GTAGCCCTGA     120
CAGCTTGGGT TTCATTTCTT TCGTGGAGCC TTGTCTCTTC CTCCCAGAAT AGGAGGAAGG     180
GAAGAGAAGG GAAAGAGGAG GGCTCTCTAG GTGAGCGCAT CAGCTGGCTC CAGCCTGAGC     240
AAGCAAGAAT TTCTTCCCA  GGAAGCTCCT CTCGCTCCCC GGCCGCCCAC CCCCAGCCTG     300
GGTGGCTGTA TCGTTTTAAC TGCATAGAGG GCAGGTCTCT TTTGGAATTA GGATTAAAGA     360
AAGTGCAGTA AAGAGAAAGC ATCGAAGACA CCATCACAAA AGATTCCCAC AACTCCATGC     420
TGTGTGCTGC AGGCTGGTCC TGAACCCAGA TCTCTGGCTG AGAGGATGGG GGCAGATGGG     480
GAAACAGTGG TTCTGAAGAA CATGCTCATT GGCGTCAACC TGATCCTTCT GGGCTCCATG     540
ATCAAGCCTT CAGAGTGTCA GCTGGAGGTC ACCACAGAAA GGGTCCAGAG ACAGTCAGTG     600
GAGGAGGAGG GAGGCATTGC CAACTACAAC ACGTCCAGCA AAGAGCAGCC TGTGGTCTTC     660
AACCACGTGT ACAACATTAA CGTGCCCTTG GACAACCTCT GCTCCTCAGG GCTAGAGGCC     720
TCTGCTGAGC AGGAGGTGAG TGCAGAAGAC GAGACTCTGG CAGAGTACAT GGGCCAGACC     780
TCAGACCACG AGAGCCAGGT CACCTTTACA CACAGGATCA ACTTCCCCAA AAAGGCCTGT     840
CCATGTTCCA GTTCAGCCCA GGTGCTGCAG GAGCTGCTGA GCCGGATCGA GATGCTGGAG     900
AGGGAGGTGT CGGTGCTGCG AGACCAGTGC AACGCCAACT GCTGCCAAGA AAGTGCTGCC     960
ACAGGACAAC TGGACTATAT CCCTCACTGC AGTGGCCACG GCAACTTTAG CTTTGAGTCC    1020
TGTGGCTGCA TCTGCAACGA AGGCTGGTTT GGCAAGAATT GCTCGGAGCC CTACTGCCCG    1080
CTGGGTTGCT CCAGCCGGGG GGTGTGTGTG GATGGCCAGT GCATCTGTGA CAGCGAGTAC    1140
AGCGGGGATG ACTGTTCCGA ACTCCGGTGC CCAACAGACT GCAGCTCCCG GGGGCTCTGC    1200
GTGGACGGGG AGTGTGTCTG TGAAGAGCCC TACACTGGCG AGGACTGCAG GGAACTGAGG    1260
TGCCCTGGGG ACTGTTCGGG GAAGGGAGA  TGTGCCACCG GTACCTGTTT ATGCGAGGAG    1320
GGCTACGTTG GTGAGGACTG CGGCCAGCGG CAGTGTCTGA ATGCCTGCAG TGGGCGAGGA    1380
CAATGTGAGG AGGGGCTCTG CGTCTGTGAA GAGGGCTACC AGGGCCCTGA CTGCTCAGCA    1440
GTTGCCCCTC CAGAGGACTT GCGAGTGGCT GGTATCAGCG ACAGGTCCAT TGAGCTGGAA    1500
TGGGACGGGC CGATGGCAGT GACGGAATAT GTGATCTCTT ACCAGCCGAC GGCCCTGGGG    1560
GGCCTCCAGC TCCAGCAGCG GGTGCCTGGA GATTGGAGTG GTGTCACCAT CACGGAGCTG    1620
GAGCCAGGTC TCACCTACAA CATCAGCGTC TACGCTGTCA TTAGCAACAT CCTCAGCCTT    1680
```

-continued

| | | | | | |
|---|---|---|---|---|---|
| CCCATCACTG | CCAAGGTGGC | CACCCATCTC | TCCACTCCTC | AAGGGCTACA | ATTTAAGACG | 1740 |
| ATCACAGAGA | CCACCGTGGA | GGTGCAGTGG | GAGCCCTTCT | CATTTTCCTT | CGATGGGTGG | 1800 |
| GAAATCAGCT | TCATTCCAAA | GAACAATGAA | GGGGGAGTGA | TTGCTCAGGT | CCCCAGCGAT | 1860 |
| GTTACGTCCT | TTAACCAGAC | AGGACTAAAG | CCTGGGGAGG | AATACATTGT | CAATGTGGTG | 1920 |
| GCTCTGAAAG | AACAGGCCCG | CAGCCCCCCT | ACCTCGGCCA | GCGTCTCCAC | AGTCATTGAC | 1980 |
| GGCCCCACGC | AGATCCTGGT | TCGCGATGTC | TCGGACACTG | TGGCTTTTGT | GGAGTGGATT | 2040 |
| CCCCCTCGAG | CCAAAGTCGA | TTTCATTCTT | TTGAAATATG | GCCTGGTGGG | CGGGGAAGGT | 2100 |
| GGGAGGACCA | CCTTCCGGCT | GCAGCCTCCC | CTGAGCCAAT | ACTCAGTGCA | GGCCCTGCGG | 2160 |
| CCTGGCTCCC | GATACGAGGT | GTCAGTCAGT | GCCGTCGAG | GGACCAACGA | GAGCGATTCT | 2220 |
| GCCACCACTC | AGTTCACAAC | AGAGATCGAT | GCCCCAAGA | ACTTGCGAGT | TGGTTCTCGC | 2280 |
| ACAGCAACCA | GCCTTGACCT | CGAGTGGGAT | AACAGTGAAG | CCGAAGTTCA | GGAGTACAAG | 2340 |
| GTTGTGTACA | GCACCCTGGC | GGGTGAGCAA | TATCATGAGG | TACTGGTCCC | CAAGGGCATT | 2400 |
| GGTCCAACCA | CCAGGGCCAC | CCTGACAGAT | CTGGTACCTG | GCACTGAGTA | TGGAGTTGGA | 2460 |
| ATATCTGCCG | TCATGAACTC | ACAGCAAAGC | GTGCCAGCCA | CCATGAATGC | CAGGACTGAA | 2520 |
| CTTGACAGTC | CCCGAGACCT | CATGGTGACA | GCCTCCTCAG | AGACCTCCAT | CTCCCTCATC | 2580 |
| TGGACCAAGG | CCAGTGGCCC | CATTGACCAC | TACCGAATTA | CCTTTACCCC | ATCCTCTGGG | 2640 |
| ATTGCCTCAG | AAGTCACCGT | ACCCAAGGAC | AGGACCTCAT | ACACACTAAC | AGATCTAGAG | 2700 |
| CCTGGGGCAG | AGTACATCAT | TTCCGTCACT | GCTGAGAGGG | GTCGGCAGCA | GAGCTTGGAG | 2760 |
| TCCACTGTGG | ATGCTTTCAC | AGGCTTCCGT | CCCATCTCTC | ATCTGCACTT | TTCTCATGTG | 2820 |
| ACCTCCTCCA | GTGTGAACAT | CACTTGGAGT | GATCCATCTC | CCCCAGCAGA | CAGACTCATT | 2880 |
| CTTAACTACA | GCCCCAGGGA | TGAGGAGGAA | GAGATGATGG | AGGTCTCCCT | GGATGCCACC | 2940 |
| AAGAGGCATG | CTGTCCTGAT | GGGCCTGCAA | CCAGCCACAG | AGTATATTGT | GAACCTTGTG | 3000 |
| GCTGTCCATG | GCACAGTGAC | CTCTGAGCCC | ATTGTGGGCT | CCATCACCAC | AGGAATTGAT | 3060 |
| CCCCCAAAAG | ACATCACAAT | TAGCAATGTG | ACCAAGGACT | CAGTGATGGT | CTCCTGGAGC | 3120 |
| CCTCCTGTTG | CATCTTTCGA | TTACTACCGA | GTATCATATC | GACCCACCCA | AGTGGGACGA | 3180 |
| CTAGACAGCT | CAGTGGTGCC | CAACACTGTG | ACAGAATTCA | CCATCACCAG | ACTGAACCCA | 3240 |
| GCTACCGAAT | ACGAAATCAG | CCTCAACAGC | GTGCGGGGCA | GGGAGGAAAG | CGAGCGCATC | 3300 |
| TGTACTCTTG | TGCACACAGC | CATGGACAAC | CCTGTGGATC | TGATTGCTAC | CAATATCACT | 3360 |
| CCAACAGAAG | CCCTGCTGCA | GTGGAAGGCA | CCAGTGGGTG | AGGTGGAGAA | CTACGTCATT | 3420 |
| GTTCTTACAC | ACTTTGCAGT | CGCTGGAGAG | ACCATCCTTG | TTGACGGAGT | CAGTGAGGAA | 3480 |
| TTTCGGCTTG | TTGACCTGCT | TCCTAGCACC | CACTATACTG | CCACCATGTA | TGCCACCAAT | 3540 |
| GGACCTCTCA | CCAGTGGCAC | CATCAGCACC | AACTTTTCTA | CTCTCCTGGA | CCCTCCGGCA | 3600 |
| AACCTGACAG | CCAGTGAAGT | CACCAGACAA | AGTGCCCTGA | TCTCCTGGCA | GCCTCCCAGG | 3660 |
| GCAGAGATTG | AAAATTATGT | CTTGACCTAC | AAATCCACCG | ACGGAAGCCG | CAAGGAGCTG | 3720 |
| ATTGTGGATG | CAGAAGACAC | CTGGATTCGA | CTGGAGGGCC | TGTTGGAGAA | CACAGACTAC | 3780 |
| ACGGTGCTCC | TGCAGGCAAC | ACAGGACACC | ACGTGGAGCA | GCATCACCTC | CACCGCTTTC | 3840 |
| ACCACAGGAG | GCCGGGTGTT | CCCTCATCCC | CAAGACTGTG | CCAGCATTT | GATGAATGGA | 3900 |
| GACACTTTGA | GTGGGGTTTA | CCCCATCTTC | CTCAATGGGG | AGCTGAGCCA | GAAATTACAA | 3960 |
| GTGTACTGTG | ATATGACCAC | CGACGGGGGC | GGCTGGATTG | TATTCCAGAG | GCGGCAGAAT | 4020 |
| GGCCAAACTG | ATTTTTTCCG | GAAATGGGCT | GATTACCGTG | TTGGCTTCGG | GAACGTGGAG | 4080 |

-continued

```
GATGAGTTCT GGCTGGGGCT GGACAATATA CACAGGATCA CATCCCAGGG CCGCTATGAG    4140
CTGCGCGTGG ACATGCGGGA TGGCCAGGAG GCCGCCTTCG CCTCCTACGA CAGGTTCTCT    4200
GTCGAGGACA GCAGAAACCT GTACAAACTC CGCATAGGAA GCTACAACGG CACTGCGGGG    4260
GACTCCCTCA GCTATCATCA AGGACGCCCT TTCTCCACAG AGGATAGAGA CAATGATGTT    4320
GCAGTGACTA ACTGTGCCAT GTCGTACAAG GGAGCATGGT GGTATAAGAA CTGCCACCGG    4380
ACCAACCTCA ATGGGAAGTA CGGGGAGTCC AGGCACAGTC AGGGCATCAA CTGGTACCAT    4440
TGGAAAGGCC ATGAGTTCTC CATCCCCTTT GTGGAAATGA AGATGCGCCC CTACAACCAC    4500
CGTCTCATGG CAGGGAGAAA ACGGCAGTCC TTACAGTTCT GAGCAGTGGG CGGCTGCAAG    4560
CCAACCAATA TTTTCTGTCA TTTGTTTGTA TTTTATAATA TGAAACAAGG GGGGAGGGTA    4620
ATAGCAATGT TTTTTGCAAC ATATTAAGAG TATGTNAAGG AAGCAGGGAT GTCGCAGGAA    4680
TCCGCTGGCT AACATCTGCT CTNGGTTTCT GCTGNCCTGG AGGC                     4724
```

( 2 ) INFORMATION FOR SEQ ID NO:4:

( i ) SEQUENCE CHARACTERISTICS:
        ( A ) LENGTH: 1358 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met Gly Ala Asp Gly Glu Thr Val Val Leu Lys Asn Met Leu Ile Gly
 1               5                  10                  15
Val Asn Leu Ile Leu Leu Gly Ser Met Ile Lys Pro Ser Glu Cys Gln
            20                  25                  30
Leu Glu Val Thr Thr Glu Arg Val Gln Arg Gln Ser Val Glu Glu Glu
        35                  40                  45
Gly Gly Ile Ala Asn Tyr Asn Thr Ser Ser Lys Glu Gln Pro Val Val
    50                  55                  60
Phe Asn His Val Tyr Asn Ile Asn Val Pro Leu Asp Asn Leu Cys Ser
65                  70                  75                  80
Ser Gly Leu Glu Ala Ser Ala Glu Gln Val Ser Ala Glu Asp Glu
            85                  90                  95
Thr Leu Ala Glu Tyr Met Gly Gln Thr Ser Asp His Glu Ser Gln Val
            100                 105                 110
Thr Phe Thr His Arg Ile Asn Phe Pro Lys Lys Ala Cys Pro Cys Ser
            115                 120                 125
Ser Ser Ala Gln Val Leu Gln Glu Leu Leu Ser Arg Ile Glu Met Leu
130                 135                 140
Glu Arg Glu Val Ser Val Leu Arg Asp Gln Cys Asn Ala Asn Cys Cys
145                 150                 155                 160
Gln Glu Ser Ala Ala Thr Gly Gln Leu Asp Tyr Ile Pro His Cys Ser
                165                 170                 175
Gly His Gly Asn Phe Ser Phe Glu Ser Cys Gly Cys Ile Cys Asn Glu
            180                 185                 190
Gly Trp Phe Gly Lys Asn Cys Ser Glu Pro Tyr Cys Pro Leu Gly Cys
        195                 200                 205
Ser Ser Arg Gly Val Cys Val Asp Gly Gln Cys Ile Cys Asp Ser Glu
    210                 215                 220
Tyr Ser Gly Asp Asp Cys Ser Glu Leu Arg Cys Pro Thr Asp Cys Ser
225                 230                 235                 240
```

```
Ser Arg Gly Leu Cys Val Asp Gly Glu Cys Val Cys Glu Glu Pro Tyr
                    245                 250                 255
Thr Gly Glu Asp Cys Arg Glu Leu Arg Cys Pro Gly Asp Cys Ser Gly
            260                 265                 270
Lys Gly Arg Cys Ala Thr Gly Thr Cys Leu Cys Glu Glu Gly Tyr Val
            275                 280                 285
Gly Glu Asp Cys Gly Gln Arg Gln Cys Leu Asn Ala Cys Ser Gly Arg
        290                 295                 300
Gly Gln Cys Glu Glu Gly Leu Cys Val Cys Glu Glu Gly Tyr Gln Gly
305                 310                 315                 320
Pro Asp Cys Ser Ala Val Ala Pro Pro Glu Asp Leu Arg Val Ala Gly
            325                 330                 335
Ile Ser Asp Arg Ser Ile Glu Leu Glu Trp Asp Gly Pro Met Ala Val
            340                 345                 350
Thr Glu Tyr Val Ile Ser Tyr Gln Pro Thr Ala Leu Gly Gly Leu Gln
            355                 360                 365
Leu Gln Gln Arg Val Pro Gly Asp Trp Ser Gly Val Thr Ile Thr Glu
        370                 375                 380
Leu Glu Pro Gly Leu Thr Tyr Asn Ile Ser Val Tyr Ala Val Ile Ser
385                 390                 395                 400
Asn Ile Leu Ser Leu Pro Ile Thr Ala Lys Val Ala Thr His Leu Ser
                405                 410                 415
Thr Pro Gln Gly Leu Gln Phe Lys Thr Ile Thr Glu Thr Thr Val Glu
            420                 425                 430
Val Gln Trp Glu Pro Phe Ser Phe Ser Phe Asp Gly Trp Glu Ile Ser
            435                 440                 445
Phe Ile Pro Lys Asn Asn Glu Gly Gly Val Ile Ala Gln Val Pro Ser
450                 455                 460
Asp Val Thr Ser Phe Asn Gln Thr Gly Leu Lys Pro Gly Glu Glu Tyr
465                 470                 475                 480
Ile Val Asn Val Val Ala Leu Lys Glu Gln Ala Arg Ser Pro Pro Thr
                485                 490                 495
Ser Ala Ser Val Ser Thr Val Ile Asp Gly Pro Thr Gln Ile Leu Val
            500                 505                 510
Arg Asp Val Ser Asp Thr Val Ala Phe Val Glu Trp Ile Pro Pro Arg
            515                 520                 525
Ala Lys Val Asp Phe Ile Leu Leu Lys Tyr Gly Leu Val Gly Gly Glu
    530                 535                 540
Gly Gly Arg Thr Thr Phe Arg Leu Gln Pro Pro Leu Ser Gln Tyr Ser
545                 550                 555                 560
Val Gln Ala Leu Arg Pro Gly Ser Arg Tyr Glu Val Ser Val Ser Ala
            565                 570                 575
Val Arg Gly Thr Asn Glu Ser Asp Ser Ala Thr Thr Gln Phe Thr Thr
            580                 585                 590
Glu Ile Asp Ala Pro Lys Asn Leu Arg Val Gly Ser Arg Thr Ala Thr
            595                 600                 605
Ser Leu Asp Leu Glu Trp Asp Asn Ser Glu Ala Glu Val Gln Glu Tyr
    610                 615                 620
Lys Val Val Tyr Ser Thr Leu Ala Gly Glu Gln Tyr His Glu Val Leu
625                 630                 635                 640
Val Pro Lys Gly Ile Gly Pro Thr Thr Arg Ala Thr Leu Thr Asp Leu
            645                 650                 655
Val Pro Gly Thr Glu Tyr Gly Val Gly Ile Ser Ala Val Met Asn Ser
            660                 665                 670
```

```
Gln Gln Ser Val Pro Ala Thr Met Asn Ala Arg Thr Glu Leu Asp Ser
        675                 680                 685

Pro Arg Asp Leu Met Val Thr Ala Ser Ser Glu Thr Ser Ile Ser Leu
    690                 695                 700

Ile Trp Thr Lys Ala Ser Gly Pro Ile Asp His Tyr Arg Ile Thr Phe
705                 710                 715                 720

Thr Pro Ser Ser Gly Ile Ala Ser Glu Val Thr Val Pro Lys Asp Arg
                725                 730                 735

Thr Ser Tyr Thr Leu Thr Asp Leu Glu Pro Gly Ala Glu Tyr Ile Ile
            740                 745                 750

Ser Val Thr Ala Glu Arg Gly Arg Gln Gln Ser Leu Glu Ser Thr Val
        755                 760                 765

Asp Ala Phe Thr Gly Phe Arg Pro Ile Ser His Leu His Phe Ser His
    770                 775                 780

Val Thr Ser Ser Ser Val Asn Ile Thr Trp Ser Asp Pro Ser Pro Pro
785                 790                 795                 800

Ala Asp Arg Leu Ile Leu Asn Tyr Ser Pro Arg Asp Glu Glu Glu Glu
                805                 810                 815

Met Met Glu Val Ser Leu Asp Ala Thr Lys Arg His Ala Val Leu Met
            820                 825                 830

Gly Leu Gln Pro Ala Thr Glu Tyr Ile Val Asn Leu Val Ala Val His
        835                 840                 845

Gly Thr Val Thr Ser Glu Pro Ile Val Gly Ser Ile Thr Thr Gly Ile
    850                 855                 860

Asp Pro Pro Lys Asp Ile Thr Ile Ser Asn Val Thr Lys Asp Ser Val
865                 870                 875                 880

Met Val Ser Trp Ser Pro Pro Val Ala Ser Phe Asp Tyr Tyr Arg Val
                885                 890                 895

Ser Tyr Arg Pro Thr Gln Val Gly Arg Leu Asp Ser Ser Val Val Pro
            900                 905                 910

Asn Thr Val Thr Glu Phe Thr Ile Thr Arg Leu Asn Pro Ala Thr Glu
        915                 920                 925

Tyr Glu Ile Ser Leu Asn Ser Val Arg Gly Arg Glu Glu Ser Glu Arg
    930                 935                 940

Ile Cys Thr Leu Val His Thr Ala Met Asp Asn Pro Val Asp Leu Ile
945                 950                 955                 960

Ala Thr Asn Ile Thr Pro Thr Glu Ala Leu Leu Gln Trp Lys Ala Pro
                965                 970                 975

Val Gly Glu Val Glu Asn Tyr Val Ile Val Leu Thr His Phe Ala Val
            980                 985                 990

Ala Gly Glu Thr Ile Leu Val Asp Gly Val Ser Glu Glu Phe Arg Leu
        995                 1000                1005

Val Asp Leu Leu Pro Ser Thr His Tyr Thr Ala Thr Met Tyr Ala Thr
    1010                1015                1020

Asn Gly Pro Leu Thr Ser Gly Thr Ile Ser Thr Asn Phe Ser Thr Leu
1025                1030                1035                1040

Leu Asp Pro Pro Ala Asn Leu Thr Ala Ser Glu Val Thr Arg Gln Ser
                1045                1050                1055

Ala Leu Ile Ser Trp Gln Pro Pro Arg Ala Glu Ile Glu Asn Tyr Val
            1060                1065                1070

Leu Thr Tyr Lys Ser Thr Asp Gly Ser Arg Lys Glu Leu Ile Val Asp
        1075                1080                1085

Ala Glu Asp Thr Trp Ile Arg Leu Glu Gly Leu Leu Glu Asn Thr Asp
```

|  | 1090 | 1095 | 1100 |
| --- | --- | --- | --- |
| Tyr Thr Val Leu Leu Gln Ala Thr Gln Asp Thr Thr Trp Ser Ser Ile | | | |
| 1105 | 1110 | 1115 | 1120 |
| Thr Ser Thr Ala Phe Thr Thr Gly Gly Arg Val Phe Pro His Pro Gln | | | |
| | 1125 | 1130 | 1135 |
| Asp Cys Ala Gln His Leu Met Asn Gly Asp Thr Leu Ser Gly Val Tyr | | | |
| | 1140 | 1145 | 1150 |
| Pro Ile Phe Leu Asn Gly Glu Leu Ser Gln Lys Leu Gln Val Tyr Cys | | | |
| | 1155 | 1160 | 1165 |
| Asp Met Thr Thr Asp Gly Gly Gly Trp Ile Val Phe Gln Arg Arg Gln | | | |
| | 1170 | 1175 | 1180 |
| Asn Gly Gln Thr Asp Phe Phe Arg Lys Trp Ala Asp Tyr Arg Val Gly | | | |
| 1185 | 1190 | 1195 | 1200 |
| Phe Gly Asn Val Glu Asp Glu Phe Trp Leu Gly Leu Asp Asn Ile His | | | |
| | 1205 | 1210 | 1215 |
| Arg Ile Thr Ser Gln Gly Arg Tyr Glu Leu Arg Val Asp Met Arg Asp | | | |
| | 1220 | 1225 | 1230 |
| Gly Gln Glu Ala Ala Phe Ala Ser Tyr Asp Arg Phe Ser Val Glu Asp | | | |
| | 1235 | 1240 | 1245 |
| Ser Arg Asn Leu Tyr Lys Leu Arg Ile Gly Ser Tyr Asn Gly Thr Ala | | | |
| 1250 | 1255 | 1260 | |
| Gly Asp Ser Leu Ser Tyr His Gln Gly Arg Pro Phe Ser Thr Glu Asp | | | |
| 1265 | 1270 | 1275 | 1280 |
| Arg Asp Asn Asp Val Ala Val Thr Asn Cys Ala Met Ser Tyr Lys Gly | | | |
| | 1285 | 1290 | 1295 |
| Ala Trp Trp Tyr Lys Asn Cys His Arg Thr Asn Leu Asn Gly Lys Tyr | | | |
| | 1300 | 1305 | 1310 |
| Gly Glu Ser Arg His Ser Gln Gly Ile Asn Trp Tyr His Trp Lys Gly | | | |
| | 1315 | 1320 | 1325 |
| His Glu Phe Ser Ile Pro Phe Val Glu Met Lys Met Arg Pro Tyr Asn | | | |
| | 1330 | 1335 | 1340 |
| His Arg Leu Met Ala Gly Arg Lys Arg Gln Ser Leu Gln Phe | | | |
| 1345 | 1350 | 1355 | |